(12) United States Patent
Flanagan (10) Patent No.: US 8,382,709 B2
(45) Date of Patent: Feb. 26, 2013

(54) DESIGNS FOR BALLOON WELDS (75) Inventor: Aiden Flanagan, Co.Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1250 days.

(21) Appl. No.: 11/526,322

(22) Filed: Sep. 25, 2006

(65) Prior Publication Data
US 2008/0077173 A1    Mar. 27, 2008

(51) Int. Cl.
*A61M 31/00* (2006.01)
*A61M 37/00* (2006.01)

(52) U.S. Cl. .............. 604/103.06; 604/103.08

(58) Field of Classification Search ........... 604/213, 604/509, 192, 194, 103.06–103.09, 96.01, 604/103; 623/1.11
See application file for complete search history.

(56) References Cited

U.S. PATENT DOCUMENTS

| | | | |
|---|---|---|---|
| 4,574,173 A | 3/1986 | Bennett | 219/10.53 |
| 4,755,649 A | 7/1988 | Barker et al. | 219/10.81 |
| 4,806,182 A | 2/1989 | Rydell et al. | 156/211 |
| 5,017,259 A | 5/1991 | Kohsai | 156/23.6 |
| 5,160,559 A | 11/1992 | Scovil et al. | 156/294 |
| 5,267,959 A | 12/1993 | Forman | 604/103 |
| 5,295,959 A | 3/1994 | Gurbel et al. | 604/96 |
| 5,304,134 A | 4/1994 | Kraus et al. | 604/96 |
| 5,458,639 A | 10/1995 | Tsukashima et al. | 604/97 |
| 5,501,759 A | 3/1996 | Forman | 156/272.8 |
| 5,545,117 A | 8/1996 | Sakamoto et al. | 493/203 |
| 5,549,557 A | 8/1996 | Steinke et al. | 604/103 |
| 5,558,737 A | 9/1996 | Brown et al. | 156/172 |
| 5,569,221 A | 10/1996 | Houser et al. | 604/282 |
| 5,772,641 A | 6/1998 | Wilson | 604/280 |
| 5,876,376 A | 3/1999 | Schwab et al. | 604/103 |
| 5,951,929 A | 9/1999 | Wilson | 604/139 |
| 5,980,505 A | 11/1999 | Wilson | 604/525 |
| 6,000,601 A | 12/1999 | Walak | 228/225 |
| 6,010,521 A | 1/2000 | Lee et al. | 606/194 |
| 6,103,037 A | 8/2000 | Wilson | 156/158 |
| 6,139,525 A | 10/2000 | Davis-Lemessy et al. | 604/103 |
| 6,168,588 B1 | 1/2001 | Wilson | 604/525 |
| 6,217,547 B1 | 4/2001 | Lee | 604/96.01 |
| 6,277,093 B1 | 8/2001 | Lee | 604/96 |
| 6,500,285 B2 | 12/2002 | Pepin et al. | 156/86 |
| 6,530,938 B1 | 3/2003 | Lee et al. | 606/194 |
| 6,699,273 B2 * | 3/2004 | Langan | 623/1.11 |

(Continued)

FOREIGN PATENT DOCUMENTS

EP    1 234 595 A2    1/2002
EP    1234595 A2    8/2002

(Continued)

*Primary Examiner* — Nicholas Lucchesi
*Assistant Examiner* — Pritesh Patel
(74) *Attorney, Agent, or Firm* — Vidas, Arrett & Steinkraus, P.A.

(57) ABSTRACT

A catheter assembly comprising a first polymer, a second polymer and a first weld region. The first polymer forms a balloon having a first waist. The second polymer forms a catheter shaft. The first waist is positioned about a portion of the catheter shaft thereby forming the first weld region. The first weld region comprises a first weld and a second weld which engage the first waist to the catheter shaft. The first weld has a first longitudinal position and the second weld has a second longitudinal position, where the first longitudinal position is different from the second longitudinal position.

15 Claims, 9 Drawing Sheets

U.S. PATENT DOCUMENTS

| | | | |
|---|---|---|---|
| 6,740,191 B2 * | 5/2004 | Clarke et al. | 604/103 |
| 6,837,897 B2 | 1/2005 | Holman et al. | 606/194 |
| 6,858,083 B2 | 2/2005 | Sterud et al. | 118/359 |
| 6,858,104 B2 * | 2/2005 | Flanagan | 156/64 |
| 6,923,787 B2 | 8/2005 | Wang | 604/96.01 |
| 6,939,321 B2 | 9/2005 | Wang et al. | 604/103.08 |
| 7,048,713 B2 | 5/2006 | Wang | 604/96.01 |
| 7,575,568 B2 * | 8/2009 | Holman et al. | 604/96.01 |
| 2001/0045257 A1 | 11/2001 | Pepin et al. | 156/158 |
| 2002/0007145 A1 | 1/2002 | Stivland et al. | 604/103.04 |
| 2002/0115963 A1 | 8/2002 | Clarke et al. | 604/103 |
| 2003/0120207 A1 | 6/2003 | Wang | 604/103.04 |
| 2003/0135231 A1 | 7/2003 | Goodin et al. | 606/192 |
| 2003/0141002 A1 | 7/2003 | Flanagan | 156/64 |
| 2003/0226631 A1 | 12/2003 | Sterud et al. | 156/64 |
| 2004/0062890 A1 | 4/2004 | Wang et al. | 428/35.2 |
| 2004/0127850 A1 | 7/2004 | Steadham et al. | 604/303 |
| 2004/0158256 A1 | 8/2004 | Chen et al. | 606/96 |
| 2004/0215141 A1 | 10/2004 | Clarke et al. | 604/103 |
| 2004/0238110 A1 | 12/2004 | Flanagan | 156/272.8 |
| 2004/0256049 A1 | 12/2004 | O'Shaughnessy et al. | 156/157 |
| 2005/0070846 A1 | 3/2005 | Wang | 604/103 |
| 2005/0119616 A1 | 6/2005 | Goodin et al. | 604/103 |
| 2005/0224471 A1 | 10/2005 | Chen | |
| 2005/0283134 A1 | 12/2005 | Chan et al. | 604/523 |
| 2006/0000812 A1 | 1/2006 | Weber et al. | 219/121.61 |
| 2006/0086701 A1 | 4/2006 | Perreault | |
| 2006/0122642 A1 | 6/2006 | Steadham et al. | 606/194 |
| 2006/0206096 A1 | 9/2006 | Accisano, III et al. | 604/540 |
| 2006/0217682 A1 | 9/2006 | Stivland et al. | 604/524 |
| 2006/0264906 A1 | 11/2006 | Pal | 604/523 |

FOREIGN PATENT DOCUMENTS

| | | |
|---|---|---|
| WO | 02/20081 A1 | 3/2002 |

* cited by examiner

DESIGNS FOR BALLOON WELDS

CROSS-REFERENCE TO RELATED APPLICATIONS

Not Applicable

STATEMENT REGARDING FEDERALLY SPONSORED RESEARCH

Not Applicable

FIELD OF THE INVENTION

In some embodiments this invention relates to the bonding of components of catheters employed in medical procedures such as angioplasty and stent delivery procedures and more particularly to a weld bonding method and weld geometries.

BACKGROUND OF THE INVENTION

Medical catheters having a balloon mounted thereon are useful in a variety of medical procedures. Balloon catheters may be used to widen a vessel into which the catheter is inserted by dilating the blocked vessel, such as in an angioplasty procedure. Balloon catheters may also be used to expand and/or seat a medical device such as a stent or graft at a desired position within a body lumen. In all of these applications, fluid under pressure may be supplied to the balloon through an inflation lumen in the catheter, thereby expanding the balloon.

It is essential in the manufacture of balloon catheters to properly seal the balloon to the catheter. The seal must be able to withstand the high pressures to which it is subjected on inflation of the balloon. A poor seal may result in leakage of inflation fluid and inability to achieve the desired pressure or even rapid loss of pressure and deflation of the balloon. In addition, it is desirable to shape the outside surface of the weld region to provide a smooth transition from the outer shaft to the balloon.

Also, in general, dilatation balloon catheters are preferably designed to optimize pushability, trackability, crossability, and torque transmission to the distal catheter end as such is applied to the proximal end of the catheter. Trackability may be defined for the purpose of this application as the ability to navigate tortuous vasculature. That is, the distal portion of the catheter preferably tracks the guide wire through small tortuous vessels to reach the area to be treated. A more flexible distal portion is known to improve such trackability. Thus, it may be desirable to provide a catheter shaft with material properties as well as a method of bonding the balloon to the catheter shaft to improve flexibility.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In order to maintain the flexibility and integrity of the catheter components, embodiments of the present invention are directed to weld geometries, configurations or constructions which minimize the reduction in flexibility caused by welding and methods which minimize the amount of heat required to create the welds so that the integrity of the catheter components are maintained after welding.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described in embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The invention is directed to weld geometries and methods to produce the inventive weld geometries. Although the figures illustrate the proximal balloon weld, the weld geometries and the methods to produce the inventive weld geometries can be applied to any catheter weld. Thus, it is within the scope of the invention for the weld configurations to be used to engage any two components of a catheter assembly where flexibility of the weld region is to be maintained. Examples of two components of a catheter assembly that may be engaged by the welds discussed herein include, but are not limited to, the distal waist of the balloon to the inner shaft, the outer shaft engaged to the inner shaft, adjacent layers of a multilayer shaft engaged to one another, a collar engaged to a sleeve, balloon, catheter shaft or another component of the catheter assembly, a sleeve engaged to a balloon, catheter shaft, or another component of the catheter assembly, and a support member engaged to a catheter shaft or another component of the catheter assembly.

For each of the weld geometries discussed herein, since each individual circumferential weld 32 is small, a smaller amount of heat input is required for the weld region 30. Thus, due to the welding geometry, less heat damage occurs at both the balloon cone 24 and at the outer shaft 20. One effect of excess heat is the crystallization of the polymer materials at and near the weld region. The crystallization causes stiffening of the catheter assembly which affects the flexibility and, therefore, the trackability, crossability and maneuverability of the catheter assembly.

Figure 1:
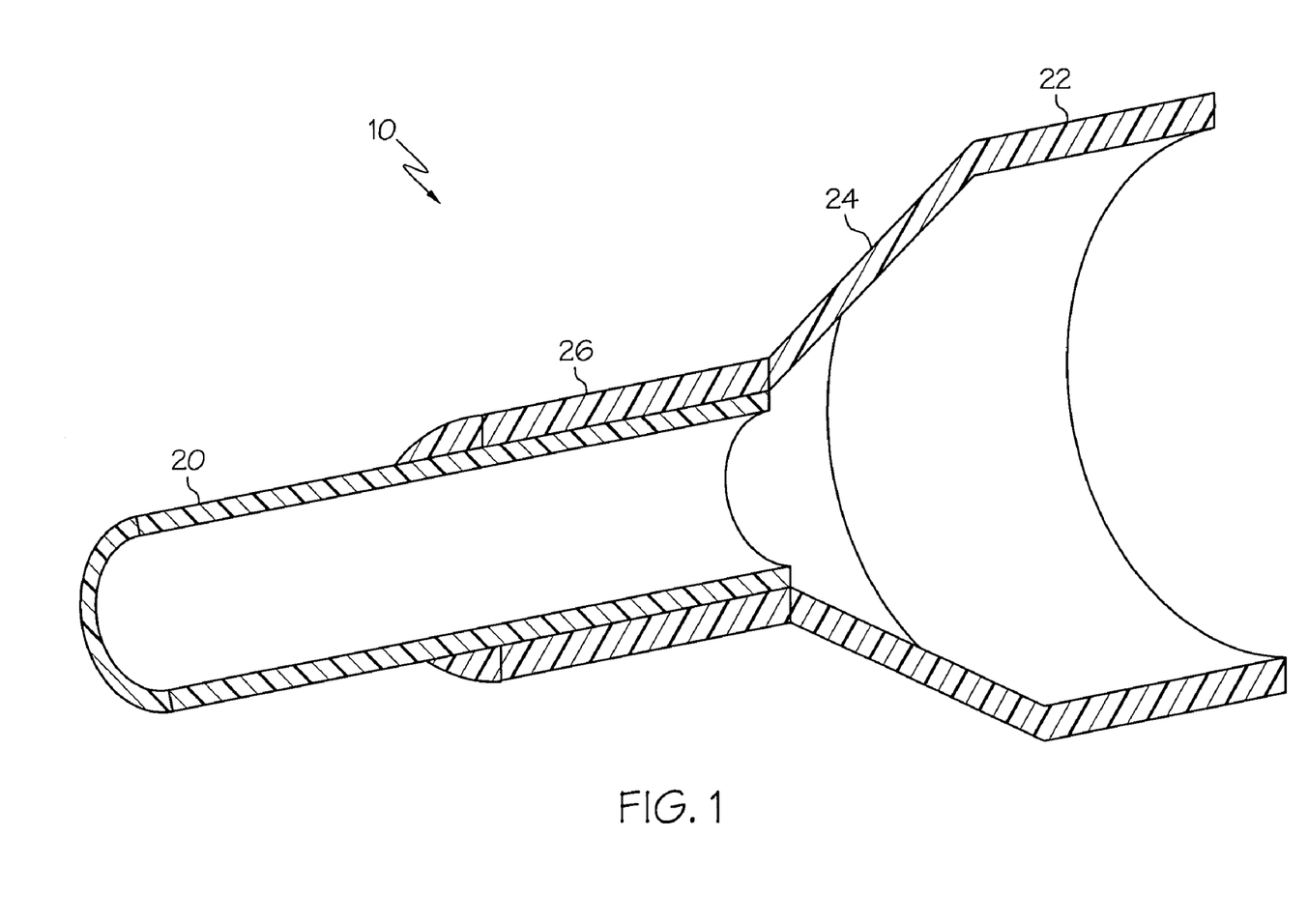
FIG. 1 is a cross-section of a typical proximal bond assembly before the weld region has been welded.
Figure 2:
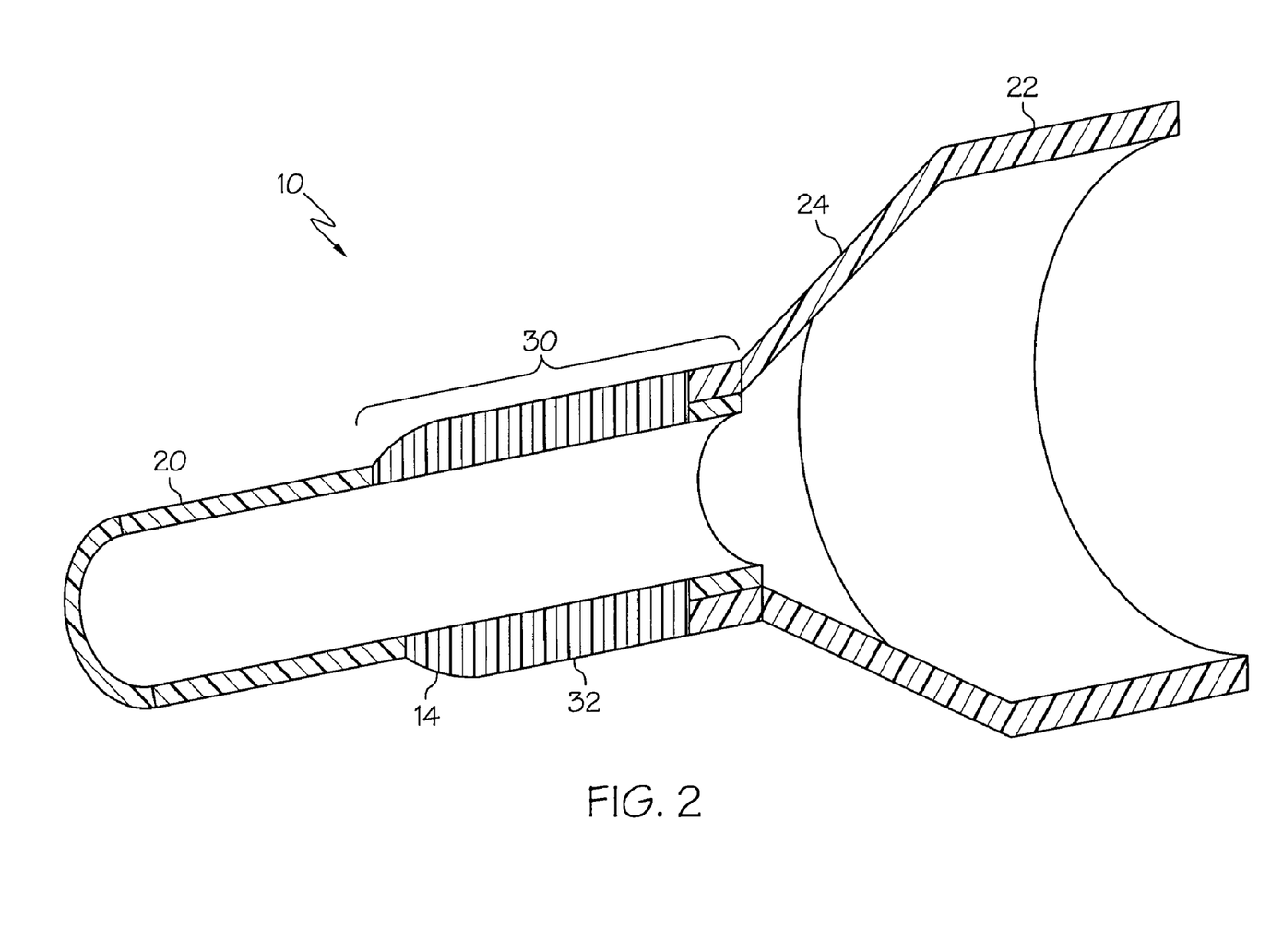
FIG. 2 is the cross-section of FIG. 1 after the PRIOR ART laser welding.

FIG. 1 illustrates a cross-section of a proximal bond assembly before welding. The catheter assembly 10 comprises an outer shaft 20 and a balloon 22. The balloon 22 has a balloon cone 24 and a balloon sleeve or waist 26. FIG. 2 is an illustration of a PRIOR ART proximal balloon weld area 30 that has one weld 32. Note that the weld 32 is continuous from the tapered proximal end region of the balloon sleeve/waist 26 to the balloon cone 24.

Figure 3:
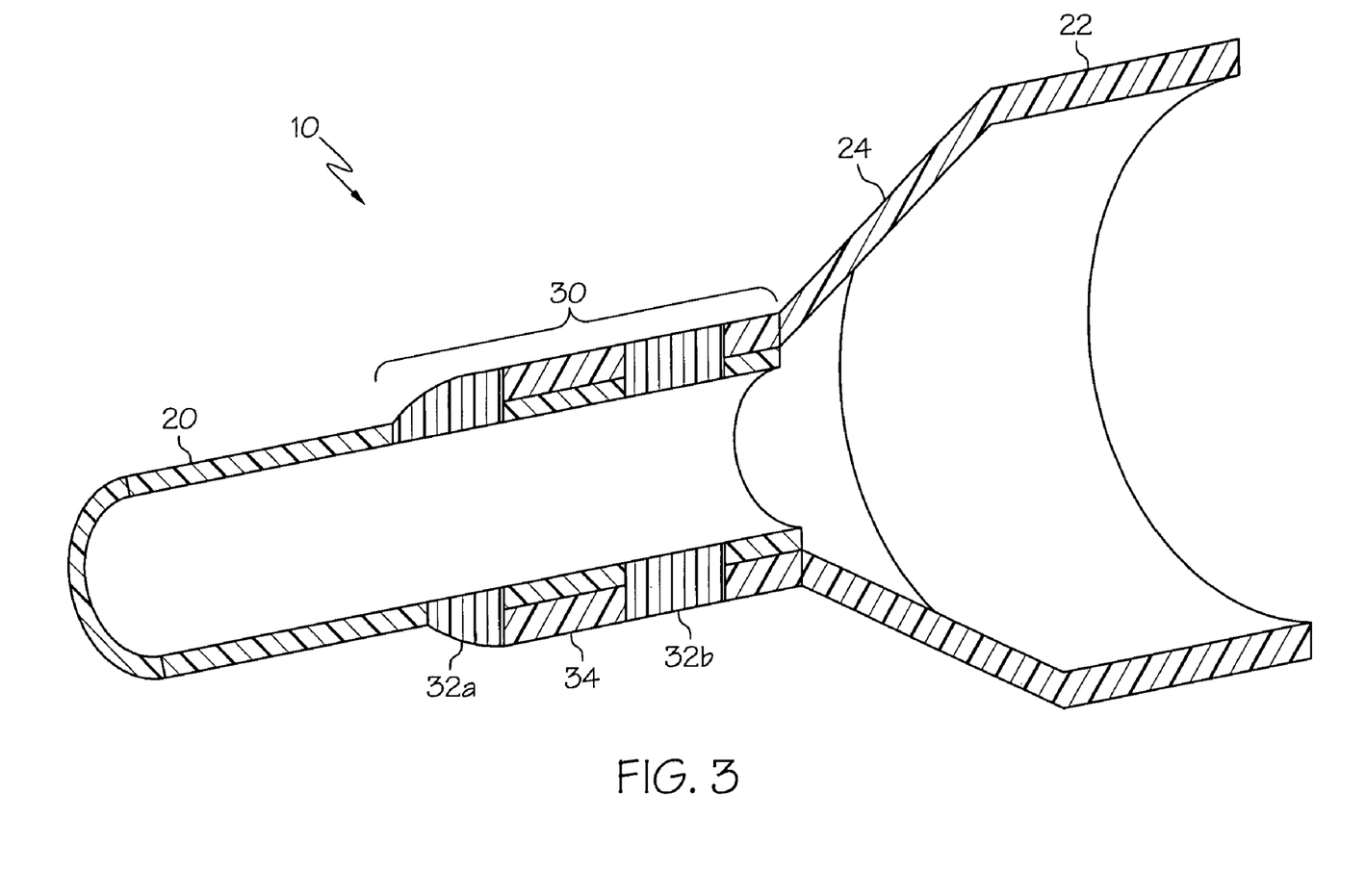
FIG. 3 is a cross-section of a weld region with two circumferential or annular welds spaced longitudinally along the catheter.

FIG. 3 illustrates a cross-section of a proximal balloon weld region 30 where the weld region 30 consists of two focal circumferential welds 32a,b which are longitudinally separated by a portion of the balloon sleeve/waist 26 and outer shaft 20 that are not welded together, i.e. the circumferential non-welded area 34. In at least one embodiment, the welds 32 have a width of less than 0.2 mm. In at least one embodiment, the welds 32 have a width less than 0.1 mm. In at least one embodiment, the circumferential non-welded area 34 is more flexible than the welds 32a,b, thereby increasing the flexibility of the distal end of the catheter assembly 10.

Figure 4:
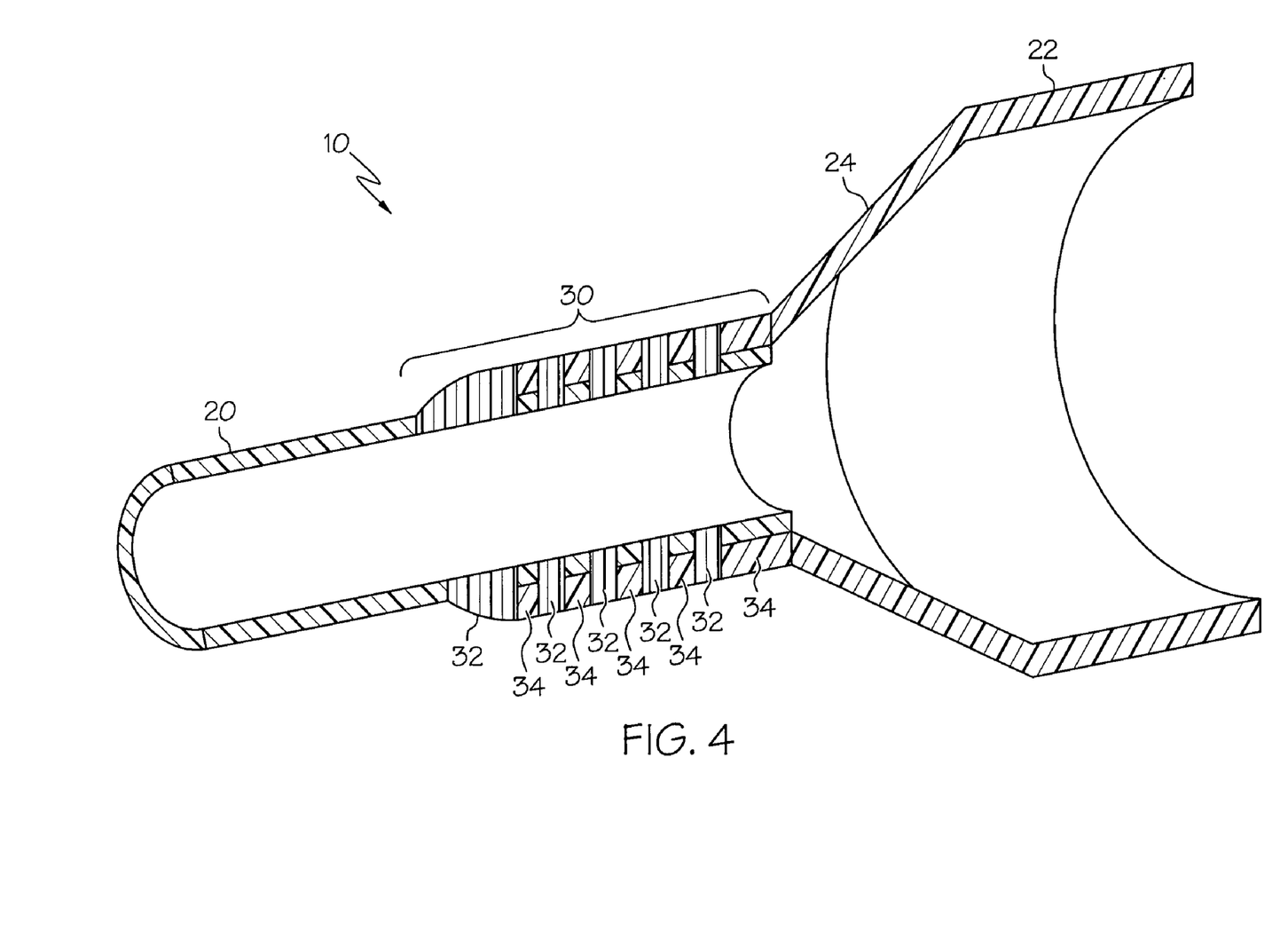
FIG. 4 is a cross-section of a weld region with a plurality of longitudinally localized focal circumferential welds.

FIG. 4 has a plurality of focal longitudinally separated circumferential welds 32 and a plurality of circumferential non-welded areas 34. It is within the scope of the invention for the weld region 30 to have two, three, four, five, six, seven, eight or more longitudinally separated circumferential welds 32.

Figure 5:
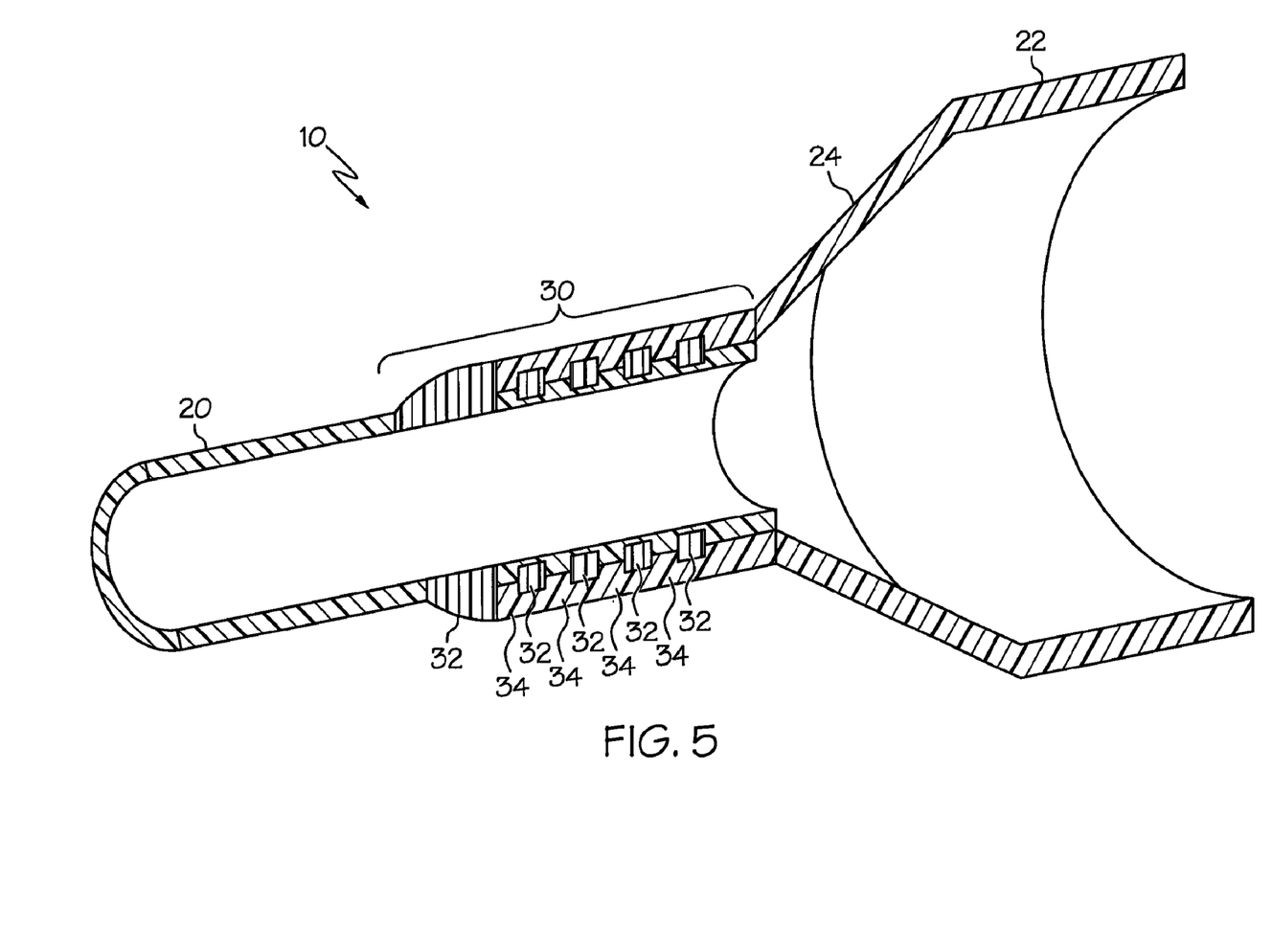
FIG. 5 is a cross-section of a weld region where the welds are localized both longitudinally and radially.

In FIG. 5, the weld region 30 has a plurality of welds 32 which are localized both longitudinally and radially. Thus, the welds 32 which are close to the balloon cone 24 are radially localized between the two polymers comprising the balloon 22 and the outer shaft 20. A radially localized weld 32 does not extend through the entire thickness of the weld region 30. Thus a radially localized weld 32 has a thickness less than the thickness of the weld region 30. Formation of radially localized welds 32 are discussed in greater detail below. Because of this radial localization, the weld 32 does not melt the outer surface of the balloon sleeve/waist 26. Further, the weld 32 that shapes the transition from the balloon sleeve/waist 26 to the outer shaft 20 is localized to the outer surface of the balloon 22 and the outer shaft 20. The non-welded areas 34 are more flexible than the welds 32, thereby increasing the flexibility of the distal end of the catheter assembly 10. Thus, in this embodiment, there is flexibility in all directions around the welds 32.

Figure 6:
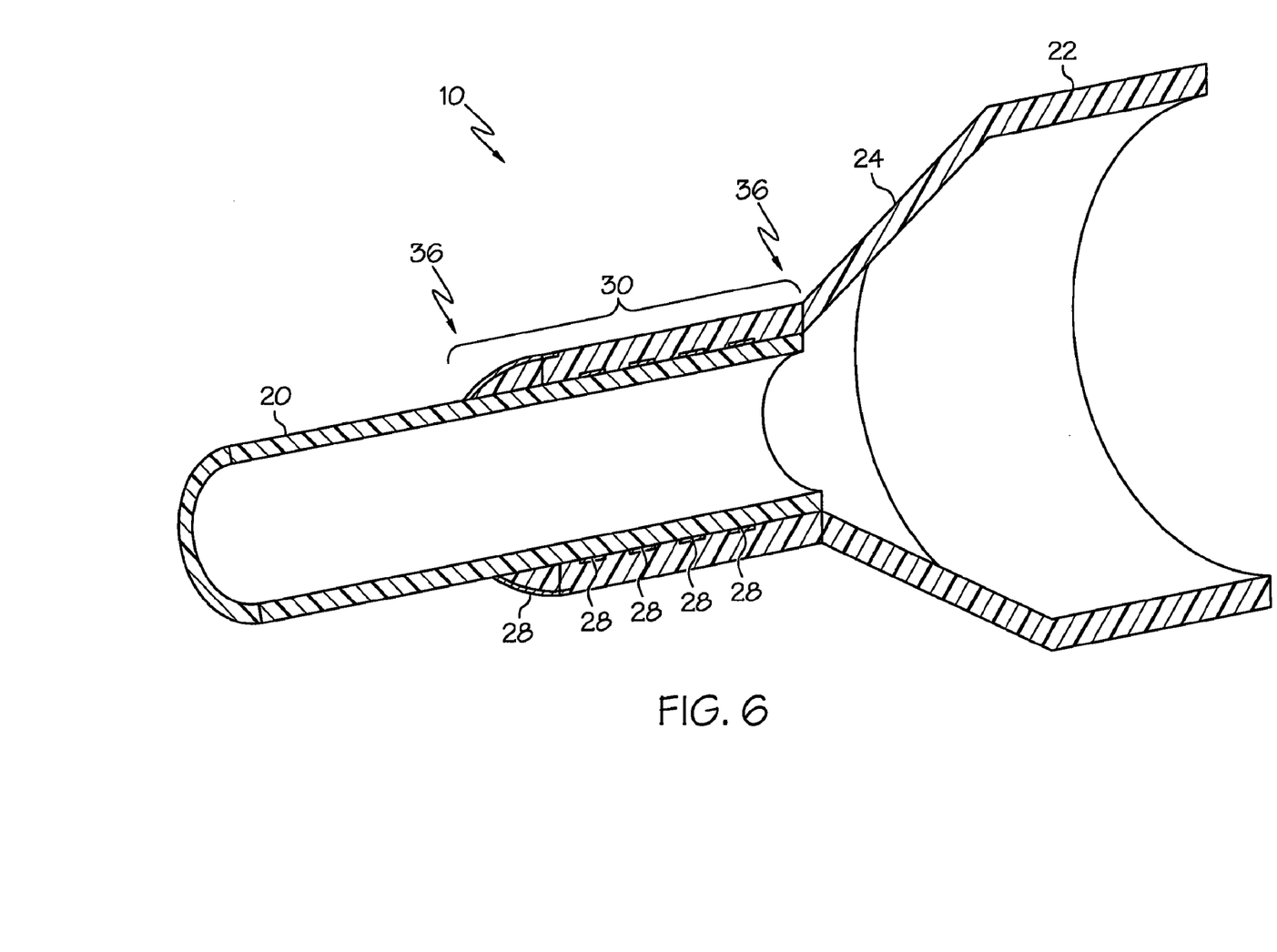
FIG. 6 is a cross-section of localized laser welding using discrete areas of absorptive material.

FIG. 6 illustrates a cross-section of a proximal bond assembly with an area of absorptive material 28 before welding. Suitable absorptive materials 28 include, but are not limited to carbon black or other carbon like graphite, and pyrolytic carbon. Absorptive materials with selective peak absorptive wavelength from 526 nm to 1097 nm include, but are not limited to, Clearweld® from Gentex, phthalocyanine, platinum dithiolene, palladium dithiolene, nickel dithiolene, anthraquinone, tris ammonium, perinone, thodamine, triarylmethine. Many of the suitable absorptive materials 28 are available from Epolin Inc., 358-364 Adams St., Newark, N.J. The areas of absorptive material 28 are positioned on the exterior surface of the proximal end of the balloon sleeve/waist 26 as well as where the balloon sleeve/waist 26 is engaged to the outer shaft 20. The welds 32 will form at the areas of absorptive material 28.

In at least one embodiment, a layer of absorptive material 28 is added at the interface between the balloon 22 polymer and the outer shaft 20 polymer. In at least one embodiment, the absorptive material 28 is positioned only at the proximal end of the proximal sleeve/waist 26 of the balloon 22. In at least one embodiment, this creates a smooth transition from the balloon sleeve/waist 26 to the outer shaft 20 without heat generation or damage to the outer shaft 20 next to the weld 32. In at least one embodiment, at least one of the catheter shafts has a region that is manufactured of absorptive material 28. In at least one embodiment, the distal end region of the outer shaft 20 is made of absorptive material 28. In at least one embodiment, the distal end region of the inner shaft is made of absorptive material 28. In at least one embodiment, the absorptive material 28 is added to the bulk material used to form the inner shaft. In at least one embodiment, the absorptive material 28 is extruded in a thin layer wherever the weld 32 is to be located, e.g. on the outer diameter of the inner shaft or on the outer diameter of the outer shaft 20. In at least one embodiment, the absorptive material 28 is painted or coated on the polymer surface where welding is desired. In the embodiment, where the absorptive material 28 is coated on a portion of the catheter, a laser is used to ablate the absorptive material 28 from the portion(s) of the catheter where a weld 32 is riot desired, thereby leaving absorptive material 28 on desired portion(s) of the catheter.

Figure 7:
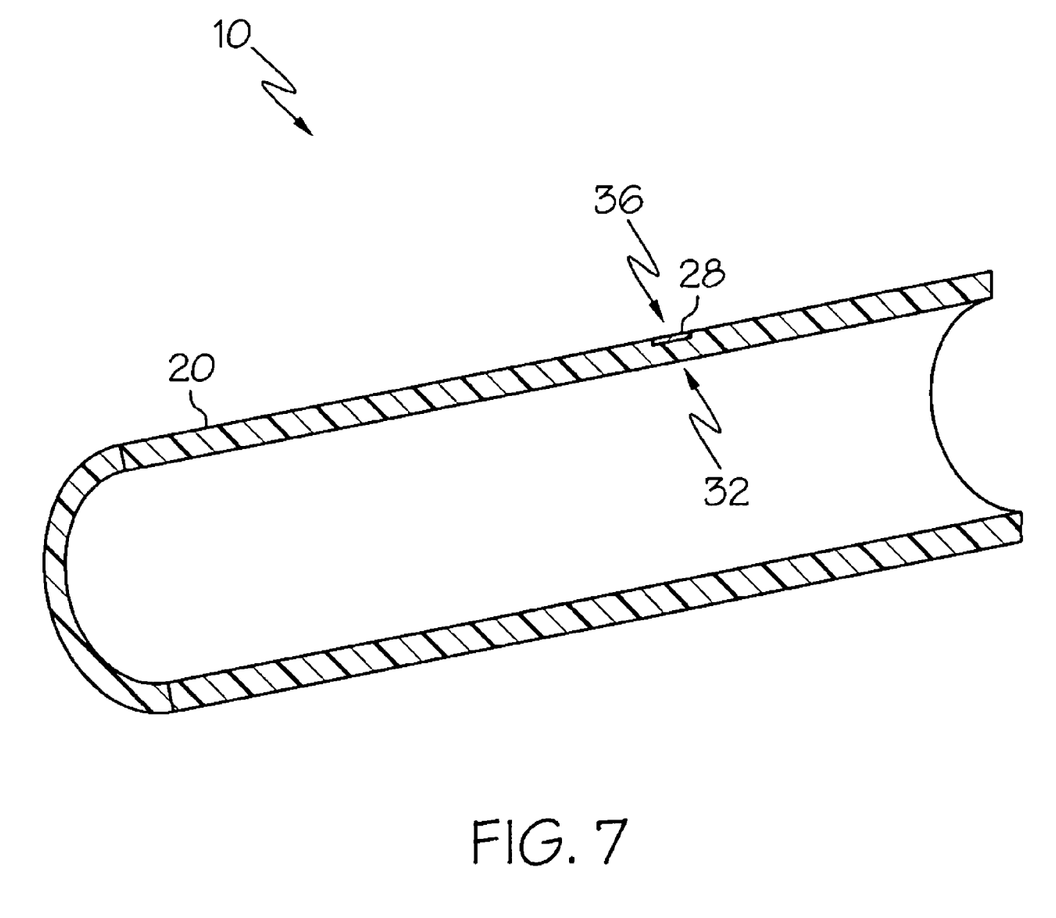
FIG. 7 is a cross-section of a portion of a weld region to be welded by a laser where scanning a laser beam activates included material that forms the pattern of absorptive areas to be bonded.

In at least one embodiment, a precursor of the absorptive material 28 is added to the bulk material used to form at least one of the inner shaft, the outer shaft 20 or to a layer of bulk material extruded where the weld 32 is to be located and illuminated with an activation wavelength to localize the absorptive material 28. Examples of suitable precursors of absorptive material, include, but are not limited to Titanium oxide ($TiO_2$) and zinc oxide (ZnO). In at least one embodiment, illustrated in FIG. 7, the absorptive areas 28 are formed when a laser beam 36 is scanned over the catheter assembly 10. In one embodiment, a UV laser is used to darken the bulk material, which contains $TiO_2$ or ZnO, in localized areas. Where the laser beam 36 is directed to the catheter assembly 10 determines where the absorptive areas 28 will be and consequently where the welds 32 will be formed on the catheter assembly 10. In at least one embodiment, the absorptive areas 28 are formed when a precursor of absorptive material is illuminated with UV light thereby turning a dark gray color.

Figure 8:
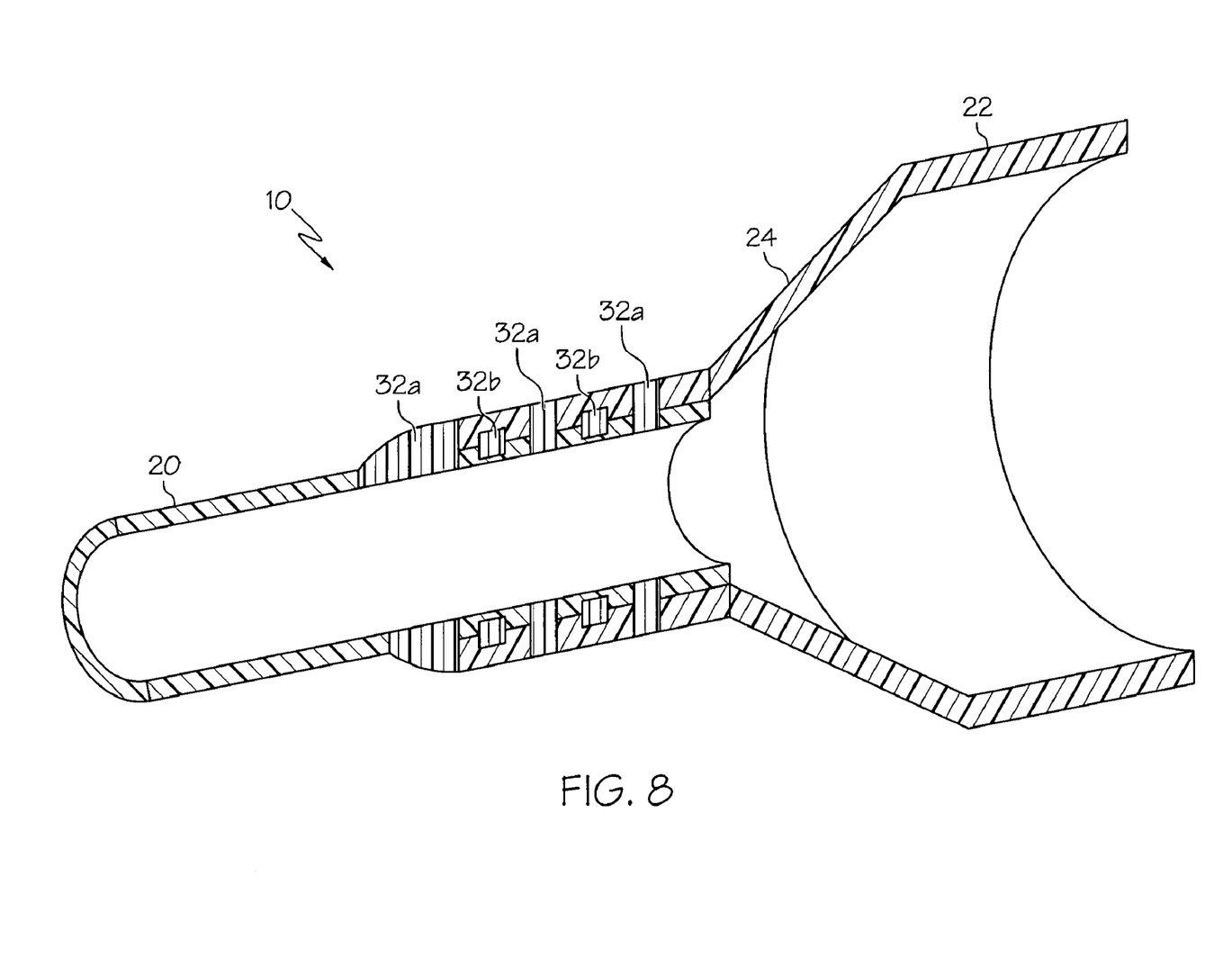
FIG. 8 is a cross-section of a weld region with both longitudinally localized focal circumferential welds and welds that are localized both longitudinally and radially.

In at least one embodiment, illustrated in FIG. 8, the weld region 30 has two types of welds 32a,b. Welds 32a are focal circumferential welds 32a which are longitudinally separated, as illustrated in FIGS. 3 and 4. Welds 32b are localized both longitudinally and radially, as illustrated in FIG. 5. In at least one embodiment, the weld region 30 has at least two types of welds 32, wherein the weld type is selected from at least one member of the group consisting of focal circumferential welds, longitudinally and radially localized welds, longitudinal line welds, spiral welds, helical welds, spot welds and any combination thereof.

The weld configurations or geometries discussed above can be achieved by several methods. Different welding methods are discussed in greater detail in U.S. Pat. No. 6,858,104 to Flanagan, U.S. Pat. No. 5,501,759 to Forman, U.S. Pat. Application 2005/0119616 to Goodin et al., U.S. Pat. No. 6,837,897 to Holman et al., U.S. Pat. No. 6,699,273 to Lanagan, U.S. Pat. No. 6,858,083 to Sterud, and U.S. Pat. No. 6,740,191 to Clarke et al., all of which are incorporated herein by reference in their entirety.

In at least one method, a section of heat shrink material is placed about the weld region. Any suitable heat shrink material may be used. Examples of suitable heat shrink material which may be used, include but are not limited to, polyethylene (e.g. polyolefin), RNF-100 which is a heat shrink tubing available from Raychem Corporation, Kynar™, nylon, polyvinalchloride, polytetrafluoroethylene and fluorinated ethylene polymer (FEP). When the section of heat shrink material is heated and thereby shrinks, it provides a force against the weld region that presses the polymer layers of the weld region together and facilitates their fusion when the welds are formed. In one embodiment, the section of heat shrink material is heated to a temperature above the shrinking temperature of the section of heat shrink material but below the melting temperature of the outer shaft polymer. In one embodiment, the section of heat shrink material is heated to a temperature between 140° C. to 180° C. In one embodiment, a laser with a wavelength almost totally absorbed by the section of heat shrink material is used to heat the section of heat shrink material. In one embodiment, a $CO_2$ laser at 10.6 microns wavelength is used to heat the section of heat shrink material. In one embodiment, microwaves are used to heat the section of heat shrink material. In one embodiment, the section of heat shrink material retains heat in the weld region during welding. In one embodiment, longitudinally focal welds are created by heat shrinking a larger section of heat shrink material and then making the focal welds within the heat shrunk length.

After the section of heat shrink material has been shrunk, a second laser is used to create the welds. This second laser has a wavelength that allows it to transmit through the heat shrink with little absorption and that is absorbed by the polymers being welded. This is known as through transmission welding. Through transmission welding is discussed in greater detail in U.S. Pat. No. 6,837,897 to Holman et al and U.S. Pat. No. 6,740,191 to Clarke et al. In at least one embodiment, the welds are formed at a temperature range of 400K to 600K (150° C. to 300° C.). The diameter of the weld will depend upon the spot size of the laser. In at least one embodiment, welds having lengths of less than 0.2 mm are made. In at least one embodiment, welds that are less than 0.1 mm are made.

In at least one embodiment, the focal circumferential welds are formed by rotating a mandrel on which the weld region is placed. In at least one embodiment, the focal circumferential welds are formed by using a second laser which is an annular welder. Thus, in this embodiment the laser rotates about the stationary weld region. Once the focal circumferential weld is created, the laser beam is turned off and moved longitudinally to the next weld position and the welding process is repeated. This process is repeated until the desired number of focal circumferential welds is created. In at least one embodiment, the focal circumferential welds 32 formed in the weld designs of FIGS. 3 and 4, are made by using a finely focused laser beam that is absorbed throughout the polymer volume. These focal circumferential welds penetrate from the outer surface of the weld region down to the mandrel.

Radially localized welds 32, such as are illustrated in FIGS. 5 and 4, are created by using a second laser with a wavelength that is almost entirely transmitted by the heat shrink used as well as by the polymers used to make the balloon and the outer shaft but which is absorbed by the absorptive layer. In at least one embodiment the laser is an Nd:YAG laser with wavelengths in the near infrared region (700-3000 nm). In at least one embodiment, the Nd:YAG laser has a spot size of approximately 580 micron (0.023 inches) diameter and a power level of approximately 0.6-0.8 watts. In at least one embodiment the laser is a Diode laser with wavelengths in the near infrared region (700-3000 nm). In at least one embodiment, the Diode laser has a spot size of approximately 580 micron (0.023 inches) diameter and a power level of approximately 0.6-0.8 watts. In at least one embodiment, the laser has a beam size of 5-10 mm, a power level of 1-5 watts and is used for a welding duration of 5 to 15 seconds. In this embodiment, the laser beam is wide enough to form several welds at once. In at least one embodiment, a finely focused laser beam is used. In order to form the radially localized weld, an absorptive layer is added in a specific location in order to localize the laser absorption, heat generation and therefore the weld location.

Figure 9:
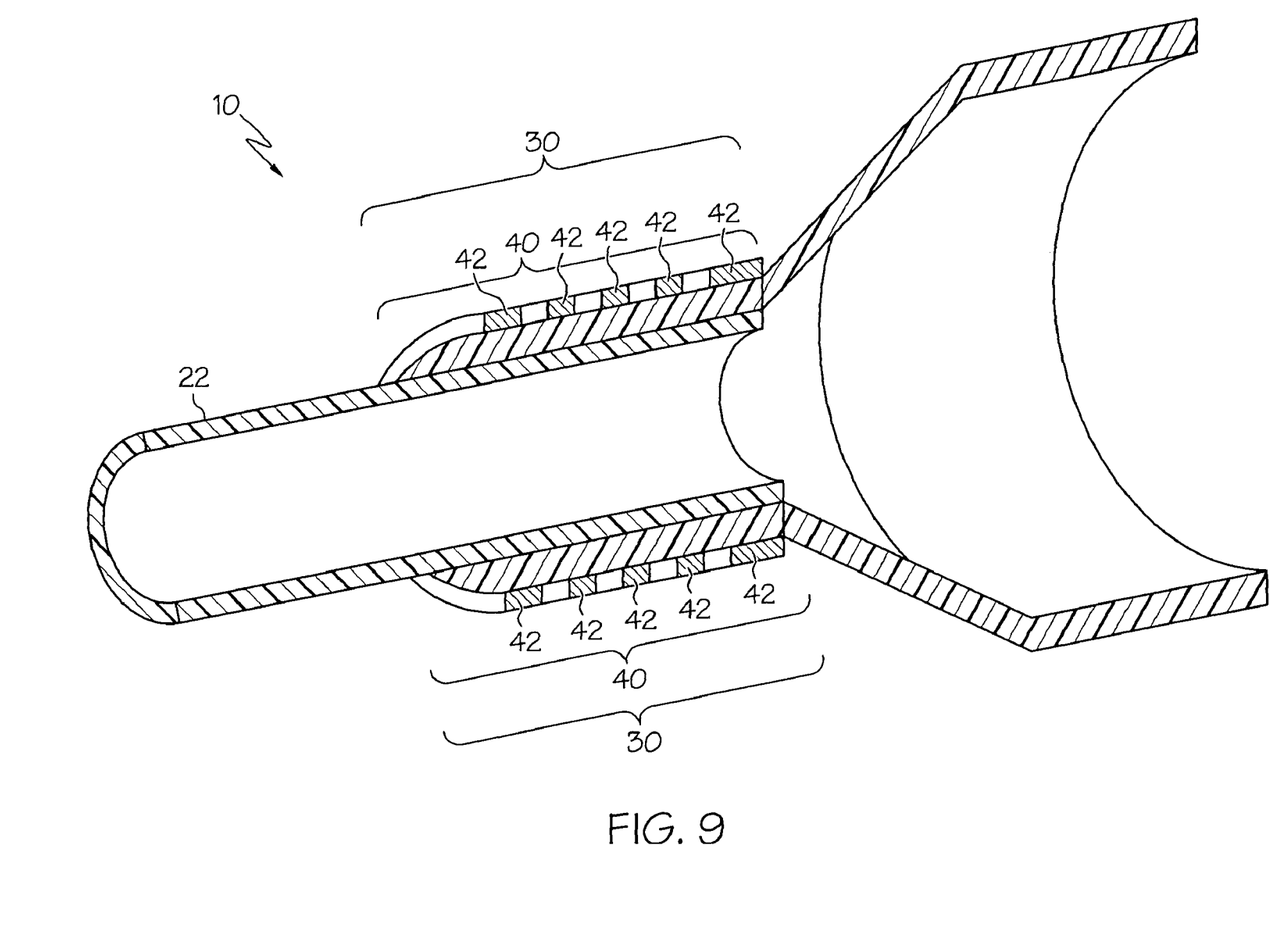
FIG. 9 is a cross-section of a weld region with heat shrink containing metal rings engaged about the weld region.

In at least one method, a section of heat shrink material 40 that has at least two metal bands 42 is used to form the welds 32, as illustrated in FIG. 9. To emphasize the position(s) of the metal bands 42, the polymeric heat shrink material 40 in FIG. 9 is not shaded. As discussed above, the section of heat shrink material 40 is placed about the weld region 30 so that when the section of heat shrink material 40 is heated it will press the two polymers (outer shaft 20 and balloon 22) together. Then microwaves are directed towards the weld region 30 covered by the section of heat shrink material 40 containing the metal bands 42. The metal bands 42 in the section of heat shrink material 40 block the microwaves so that welds 32 are not formed in the areas underneath the metal bands while the portions of the weld region 30 not covered by the at least two metal bands 42 will form welds 32.

In at least one embodiment, radio frequency induction is used to form welds 32 when a section of heat shrink material 40 with at least two metal bands 42 is placed about the weld region 30, as illustrated in FIG. 9. The number of metal bands 42 in the section of heat shrink material 40 depends upon the number of welds 32 desired. Thus, it is within the scope of the invention for the section of heat shrink material 40 to have one, two, three, four, five, six, seven, eight or more metal bands 42. In at least one embodiment, the mandrel has small rings of material positioned in locations where a weld is desired, which is discussed in greater detail in U.S. Pat. No. 6,858,083 to Sterud. The small rings of material may be made of, for example, but not limited to 17-4 PH stainless steel, which has the property of heating up to a greater extend and more quickly than other metals when exposed to the RF field. In these embodiments, a radio-frequency (RF) current generator generates a RF current which is controllably used to create a magnetic field within a magnetic flux concentrator. The at least two metal bands 42 in the heat shrink material 40, or in the mandrel, generates induction heating at its surface when exposed to the magnetic flux. The heat at the surface of the at least two metal bands 42 is transferred to the weld region 30 and a weld is formed underneath the at least two metal bands 42. The weld region 30 after welding is shown in FIG. 4.

While utilizing the methods described herein to make the welds, the temperature of the weld region can be regulated by using an infrared detector or sensor, as discussed in U.S. Pat. No. 6,858,104 to Flanagan and in U.S. Pat. No. 6,858,083 to Sterud, both of which are incorporated herein by reference in their entirety. Briefly, the infrared detector or sensor detects the thermal radiation being emitted from the weld region and provides feedback to the laser in order to control the output of the laser beam or the radio-frequency current generator. Any infrared detector is suitable but it is preferable that an infrared detector be selected that is sensitive to infrared readings as they are emanated from polymeric materials at around their melting temperatures. In at least one embodiment, due to the small weld areas of the weld designs, an infrared radiation collector is used to get an accurate reading in low infrared emission situations. The infrared radiation collector enhances the signal to noise ratio of the detected infrared radiation. In at least one embodiment, the infrared detector is used with an infrared radiation collector, an optical chopper and a lock-in amplifier.

Polymeric materials that may be used for the shafts of balloon catheters include, but are not limited to, high density polyethylene (HDPE), polyamides, the polyetheramide copolymer family, HDPE with and without compatibilizers, low density polyethylene (LDPE), LDPE with and without compatibilizers, linear low density polyethylene (LLDPE), LLDPE with and without compatibilizers, polyethylene copolymers such as ethylene vinyl acetate copolymer (EVA) and other vinyl acetates, urethanes, polybutylene terephthalate (PBT), thermoplastic elastomers, isonomers, ethylene acrylic acid polymers, polyether block amide, and ethylene acrylic acid copolymer (EAA), polyurethane, polyesters such as polyethylene terephthalate (PET), polybutylene terephthalate (PBT), copolyesters such as Hytrel, other thermoplastic elastomers such as thermoplastic polyolefin (TPO), styrenic thermoplastic elastomers such as C-Flex, and ionomers such as Surlyn and any combination thereof.

Polymer materials that can be used for balloons include, but are not limited to, ethylene-vinyl acetate, polyvinyl chloride(PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins, polyethylene terephthalates, polyacrylenesulfide, and copolyesters, nylon, and polyamines. Other balloon materials may also be used.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

The following numbered statements characterize embodiments and methods of the invention:

1. A method for forming a weld region with at least two longitudinally localized welds comprising the steps of:
   providing a weld region, the weld region comprising a first polymer, a second polymer and having a longitudinal length;
   providing a section of heat shrink material, the section of heat shrink material having at least two metal bands;
   placing the section of heat shrink material on the weld region;
   heating the section of heat shrink material to a temperature above the shrinking temperature of the section of heat shrink material so that the section of heat shrink material presses the first polymer to the second polymer; and
   creating at least two welds by directing microwaves towards the section heat shrink material, the at least two metal bands blocking the microwaves so that the at least two welds are formed between the at least two metal bands.

2. The method of statement 1 further comprising the steps of:
   providing a infrared temperature measurement device; and
   monitoring the temperature of the weld region with the infrared temperature measurement device;

3. A method for forming a weld region with at least two longitudinally localized welds comprising the steps of:
   providing a weld region, the weld region comprising a first polymer, a second polymer and having a longitudinal length;
   providing a section of heat shrink material, the section of heat shrink material having at least two metal bands;
   placing the section of heat shrink material on the weld region;
   heating the section of heat shrink material to a temperature above the shrinking temperature of the section of heat shrink material so that the section of heat shrink material presses the first polymer to the second polymer; and
   creating at least two welds by using radio frequency induction wherein an electromagnetic wave passes through the at least two metal bands in the section of heat shrink material, thereby causing an electric current which forms the at least two welds.

4. The method of statement 3, further comprising the steps of:
   providing a infrared temperature measurement device; and
   monitoring the temperature of the weld region with the infrared temperature measurement device.

5. A method for forming a weld region with at least two longitudinally and radially localized welds comprising the steps of:
   providing a weld region, the weld region comprising a first polymer, a second polymer, an absorptive material and having a longitudinal length;
   providing a section of heat shrink material;
   providing a first laser, the first laser having a wavelength that is transmitted through the section of heat shrink material, the first polymer and the second polymer and absorbed by the absorptive material;
   placing the section of heat shrink material on the weld region;
   rotating the weld region;
   heating the section of heat shrink material to a temperature above the shrinking temperature of the section of heat shrink material so that the section of heat shrink material presses the first polymer to the second polymer;
   turning on the first laser;
   creating a first weld with the first laser focused on a first position along the longitudinal length of the weld region where the first weld is desired, the heat generated when the first laser hits the absorptive material forming a weld;
   turning off the first laser;
   moving the first laser to a second position along the longitudinal length of the weld region where a second weld is desired, the second position different from the first position; and
   creating a second weld with the first laser focused on the second position and heating the first and second polymer until a weld is formed.

6. The method of statement 5, further comprising the steps of:
   providing a infrared temperature measurement device to monitor the temperature of the weld region; and
   monitoring the temperature of the weld region with the infrared temperature measurement device;

7. The method of statement 5, wherein the first and second welds are circumferential welds, the circumferential welds created by rotating the weld region, the weld region rotated by a mandrel.

8. The method of statement 5, wherein the first and second welds are circumferential welds, the circumferential welds created by using a first laser that rotates about the weld region.

9. The method of statement 5, wherein the section of heat shrink material is heated by a second laser, the second laser emitting a wavelength absorbed by the section of heat shrink material.

10. The method of statement 5, wherein the section of heat shrink material is heated by microwaves.

11. The method of statement 5, wherein the absorptive material is a layer positioned between the first polymer and the second polymer.

12. The method of statement 5, wherein the absorptive material is the first polymer.

13. The method of statement 5, wherein the weld region has at least two sections of absorptive material, the at least two sections of absorptive material each having a different longitudinal position.

14. The method of statement 5, the first polymer having a surface, wherein the at least two sections of absorptive material are painted or coated on the surface of the first polymer at positions were welds are desired.

15. The method of statement 5, wherein the absorptive material is extruded in a thin layer where a weld is desired.

16. The method of statement 5, wherein the first polymer comprises a precursor of the absorptive material, the precursor transforming into absorptive material when illuminated with an activation wavelength.

17. The method of statement 16, wherein the precursor of the absorptive material is a material that when illuminated with ultraviolet light turns a dark gray color.

18. The method of statement 16, wherein the precursor is an electrochromic material selected from at least one member of the group consisting of titanium oxide, zinc oxide, viologens and any combination thereof.

19. The method of statement 5, wherein a precursor of the absorptive material is extruded in a thin layer where a weld is desired, the precursor layer illuminated with an activation wavelength to form the absorptive material.

20. The method of statement 5, wherein the second laser is selected from the group consisting of an Nd:YAG laser or a Diode laser with wavelengths in the near infrared region.

21. The method of statement 5, wherein the absorptive material is selected from at least one member of the group consisting of carbon black, graphite, pyrolytic carbon, phthalocyanine, platinum dithiolene, palladium dithiolene, nickel dithiolene, anthraquinone, tris ammonium, perinone, thodamine, triarylmethine, and any combination thereof.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A catheter assembly comprising a first polymer, a second polymer and a first weld region, the first polymer forming a balloon, the balloon having a first waist, the second polymer forming a catheter shaft, the first waist positioned about a portion of the catheter shaft thereby forming the first weld region, the first weld region comprising a first weld and a second weld, the first weld and the second weld engaging the first waist to the catheter shaft, the first weld having a first longitudinal position, the second weld having a second longitudinal position, the first longitudinal position different from the second longitudinal position, the first weld region further comprising a first non-weld area having a third longitudinal position, the third longitudinal position being between the first and second longitudinal positions.

2. The catheter assembly of claim 1, wherein the first and second welds are circumferential welds.

3. The catheter assembly of claim 2, the first weld region having a thickness, the first weld and second weld each having a thickness, the thickness of the first and second welds at most equal to the thickness of the first weld region.

4. The catheter assembly of claim 3, the thickness of the first weld different than the thickness of the second weld.

5. The catheter assembly of claim 1, further comprising at least one weld selected from at least one member of the group consisting of longitudinal line welds, spiral welds, helical welds, spot welds and any combination thereof.

6. The catheter assembly of claim 1, further comprising at least one more weld, each of the at least one more weld having a longitudinal position different than both the first and second longitudinal positions.

7. A catheter assembly comprising a first polymer, a second polymer and a first weld region, the first weld region comprising a first weld and a second weld, the first weld and second weld engaging the first polymer and the second polymer, the first weld having a first longitudinal position and a first thickness, the second weld having a second longitudinal position and a second thickness, the first longitudinal position different from the second longitudinal position, the first weld region having a thickness, the first thickness and second thickness being at most equal to the thickness of the weld region, and the first thickness being different than the second thickness.

8. The catheter assembly of claim 7, the first and second welds being circumferential.

9. The catheter assembly of claim 7, further comprising at least one more weld, each of the at least one more weld having a longitudinal position different than both the first and second longitudinal positions, and the at least one weld having a thickness at most equal to the thickness of the weld region.

10. A catheter assembly comprising a first polymer, a second polymer and a first weld region, the first polymer forming a balloon, the balloon having a first waist, the second polymer forming a catheter shaft, the first waist positioned about a portion of the catheter shaft thereby forming the first weld region, the first weld region comprising a plurality of welds engaging the balloon and the catheter shaft together, each of the plurality of welds having a different longitudinal position, the first weld region having a thickness, each of the plurality of welds having a thickness, the thickness of each of the plurality of welds at most equal to the thickness of the first weld region.

11. The catheter assembly of claim 10, each of the plurality of welds being circumferential welds.

12. The catheter assembly of claim 10, the thickness of at least one of the plurality of welds being different than the thickness of the other welds.

13. The catheter assembly of claim 10, the plurality of welds being at least three welds.

14. The catheter assembly of claim 10, the plurality of welds being at least four welds.

15. A catheter assembly comprising a first polymer, a second polymer and a first weld region, the first polymer forming a balloon, the balloon having a first waist, the second polymer forming a catheter shaft, the first waist positioned about a portion of the catheter shaft thereby forming the first weld region, the first weld region comprising a first weld and a second weld, the first weld and the second weld engaging the first waist to the catheter shaft, the first weld having a first longitudinal position, the second weld having a second longitudinal position, the first longitudinal position different from the second longitudinal position;

wherein the first and second welds are circumferential welds, the first weld region having a thickness, the first weld and second weld each having a thickness, the thickness of the first and second welds at most equal to the thickness of the first weld region.

* * * * *

UNITED STATES PATENT AND TRADEMARK OFFICE
CERTIFICATE OF CORRECTION

| | | |
|---|---|---|
| PATENT NO. | : 8,382,709 B2 | Page 1 of 1 |
| APPLICATION NO. | : 11/526322 | |
| DATED | : February 26, 2013 | |
| INVENTOR(S) | : Flanagan | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1653 days.

Signed and Sealed this
Eighth Day of October, 2013

Teresa Stanek Rea
*Deputy Director of the United States Patent and Trademark Office*